United States Patent
Höpcke et al.

(10) Patent No.: US 6,646,112 B2
(45) Date of Patent: Nov. 11, 2003

(54) DEHYDRATED DEXTROSE MONOHYDRATE, PREPARATION AND USE THEREOF

(75) Inventors: Reiner Höpcke, Kleve (DE); Richard James Tippett, Krefeld (DE); Christof Küsters, Krefeld (DE)

(73) Assignee: Cerestar Holding B.V., LA Sas van Gent (NL)

( * ) Notice: Subject to any disclaimer, the term of this patent is extended or adjusted under 35 U.S.C. 154(b) by 91 days.

(21) Appl. No.: 09/950,809

(22) Filed: Sep. 13, 2001

(65) Prior Publication Data

US 2002/0188113 A1 Dec. 12, 2002

(30) Foreign Application Priority Data

Sep. 13, 1999 (GB) .............................. 0022522

(51) Int. Cl.⁷ ............................ C07H 15/04; C07H 1/00
(52) U.S. Cl. ................... 536/18.6; 536/4.1; 536/18.5; 536/120; 536/124
(58) Field of Search ................. 536/120, 124, 536/18.5, 4.1, 18.6

(56) References Cited

U.S. PATENT DOCUMENTS

| 4,950,743 A | * 8/1990 | McCurry, Jr. et al. |
| 5,554,741 A | 9/1996 | Carduck et al. |
| 5,886,161 A | 3/1999 | Oka et al. |

FOREIGN PATENT DOCUMENTS

| DE | 4204699 A1 | 8/1993 |
| DE | 4 207 101 A1 | 9/1993 |
| DE | 19710112 | 9/1998 |
| EP | 0 319 616 A1 | 6/1989 |
| IN | 121162 | * 7/1971 |
| WO | WO 93/16088 | 8/1993 |
| WO | WO 98/40391 | 9/1998 |

OTHER PUBLICATIONS

Abstract to IN 121162, SHAH, Jul. 1971. (Abstract Sent).*

* cited by examiner

Primary Examiner—Samuel Barts
Assistant Examiner—Michael C. Henry
(74) Attorney, Agent, or Firm—Fitch, Even, Tabin & Flannery

(57) ABSTRACT

The present invention relates to dehydrated dextrose monohydrate having a specific surface area of from 0.20 $m^2/g$ to 0.50 $m^2/g$ and is reducing the reaction time for preparing chemical compounds selected from the group consisting of alkyl glucoside, alkenyl glucoside, alkyl polyglucosides and alkenyl polyglucosides in a heterogeneous mixture with an alcohol. The present invention further discloses a process for preparing dehydrated dextrose monohydrate and a process for preparing chemical compounds selected from the group consisting of alkyl glucoside, alkenyl glucoside, alkyl polyglucosides and alkenyl polyglucosides by applying dehydrated dextrose monohydrate.

20 Claims, 4 Drawing Sheets

Dehydrated dextrose monohydrate

Crystallised anhydrous dextrose

Dehydrated dextrose monohydrate

Crystallised anhydrous dextrose

DEHYDRATED DEXTROSE MONOHYDRATE, PREPARATION AND USE THEREOF

TECHNICAL FIELD

The present invention relates to a process for the preparation of chemical compounds such as alkyl glucoside, alkenyl glucoside, alkyl polyglucosides and/or alkenyl polyglucosides wherein the reaction time of said process is reduced by applying dehydrated dextrose monohydrate in a heterogeneous reaction.

BACKGROUND OF THE INVENTION

The reaction of a reducing saccharide, e.g. an aldose or ketose, or a source thereof, with an alcohol results in the formation of a glycoside. Acids catalyse the reaction between a reducing saccharide and an alcohol. When the alcohol is an alkanol, the resulting glycoside is commonly referred to as an alkyl glycoside.

It is general knowledge to conduct the reaction under substantially anhydrous conditions in order to shift the chemical equilibrium to the reaction products and to avoid side-reactions such as de-acetalisation, formation of substantial quantities of undesired higher polysaccharide by-products e.g. polydextrose, and the formation of coloured bodies.

EP 0319616 describes a process for preparing glycoside products by the direct acid catalysed reaction of an aqueous saccharide solution or syrup with an alcohol reactant and without the generation of substantial quantities of undesired polysaccharide by-products by conducting said reaction in a way which prevents any aqueous saccharide solution from coming into contact with the acid catalyst during said reaction under conditions conductive to homopolymerisation of said saccharide reactant. However, this process requires a specialised set-up and the drying process has a negative effect on the quality and composition of the water-free products.

DE 42 04 699 relates to a process for producing water-free aldoses wherein aqueous syrups of starch-based products are mixed with a fatty alcohol and the total mixture is brought in a turbo-dryer at a drying temperature of between 160° C. and 180° C. for obtaining a melt of water-free dextrose. However, besides the melt of the water-free glucose, there is a second fraction, which is containing fatty alcohol and water that has been removed from the aqueous solution of the starch-based product. Due to the presence of water, this fatty alcohol cannot be used directly in the further processing.

DE 42 07 101 describes a process for producing alkyl and/or alkenyl glucosides wherein an aqueous solution of glucose syrup and fatty alcohol is brought into a turbo-dryer for dehydration until residual water-content of 0.05 to 0.3% is reached, followed by acetalisation in presence of acid catalyst.

DE 197 10 112 relates to a continuous process for preparing alkyl and/or alkenyl-oligoglycosides with excess of alcohol and glucose in solid form and wherein said process is performed in a reactor-cascade.

In general, dextrose monohydrate is applied for producing alkyl glucosides, and prior to the acetalisation reaction, the crystal-water of the monohydrate is removed during heating of the reaction mixture in the reactor. At least 10%, but most of the time 30% or even more of the capacity of the reactor is used for dehydration instead of the acetalisation reaction.

There is a need for an economically viable process for preparing alkyl glucosides with relative cheap dry reactants and wherein the reaction time of said process is short, and the formation of undesired by-products is reduced.

The current invention provides such a process.

SUMMARY OF THE INVENTION

The present invention relates to dehydrated dextrose monohydrate with a specific surface area of from 0.20 $m^2/g$ to 0.50 $m^2/g$ and which reduces the reaction time for preparing chemical compounds selected from the group consisting of alkyl glucoside, alkenyl glucoside, alkyl polyglucosides and alkenyl polyglucosides in a heterogeneous mixture with an alcohol. In fact, said reaction time is reduced with at least 10%, preferably 20%, more preferably 25%, most preferably with 50%.

The current invention further relates to a process for preparing chemical compounds selected from the group consisting of alkyl glucoside, alkenyl glucoside, alkyl polyglucosides and alkenyl polyglucosides wherein in said process an alcohol is reacting in a heterogeneous mixture with dehydrated dextrose monohydrate disclosed in the present invention.

The present invention relates to a process wherein the alcohol has an alkyl or alkenyl chain length selected from the group consisting of $C_1$ to $C_{30}$ and mixtures thereof.

The present invention further relates to a process, which is comprising the following steps:

a) adding dehydrated dextrose monohydrate to an alcohol containing liquid for obtaining a heterogeneous mixture,
b) Stirring the heterogeneous mixture,
c) Heating under vacuum to a temperature between 60° C. to 180° C., preferably between 80° C. to 150° C., more preferably between 95° C. to 120° C.,
d) Adding acid catalyst,
e) Continuing stirring at high temperature under vacuum until level of residual dehydrated dextrose monohydrate is below desired value.
f) Optionally neutralising of acid catalyst, and
g) Optionally evaporating the excess of liquid containing alcohol.

The current invention discloses a process wherein:

a) 1 weight-part of dehydrated dextrose monohydrate is added to from 2 to 10 weight-parts of $C_6$–$C_{25}$ alcohol for obtaining a heterogeneous mixture,
b) The heterogeneous mixture is heated to 80–180° C., while stirring at 5 to 400 mbar vacuum,
c) 0.2–5% w/w (based on dry substance of dehydrated dextrose monohydrate) acid catalyst is added,
d) Continuing stirring at high temperature under vacuum until the amount of residual dehydrated dextrose monohydrate is below desired value.

The current invention further relates to a process for preparing dehydrated dextrose monohydrate by drying dextrose monohydrate wherein said dehydrated dextrose monohydrate has a specific surface area of from 0.2 $m^2/g$ to 0.50 $m^2/g$ and it reduces the reaction time for preparing in a heterogeneous reaction with an alcohol chemical compounds selected from the group consisting of alkyl glucoside, alkenyl glucoside, alkyl polyglucosides and alkenyl polyglucosides, and said process comprises the following steps:

a) Taking dextrose monohydrate, b) Drying dextrose monohydrate at a temperature between 50 to 150° C., c) Collecting dehydrated dextrose monohydrate.

DETAILED DESCRIPTION OF THE INVENTION

Figure 1:
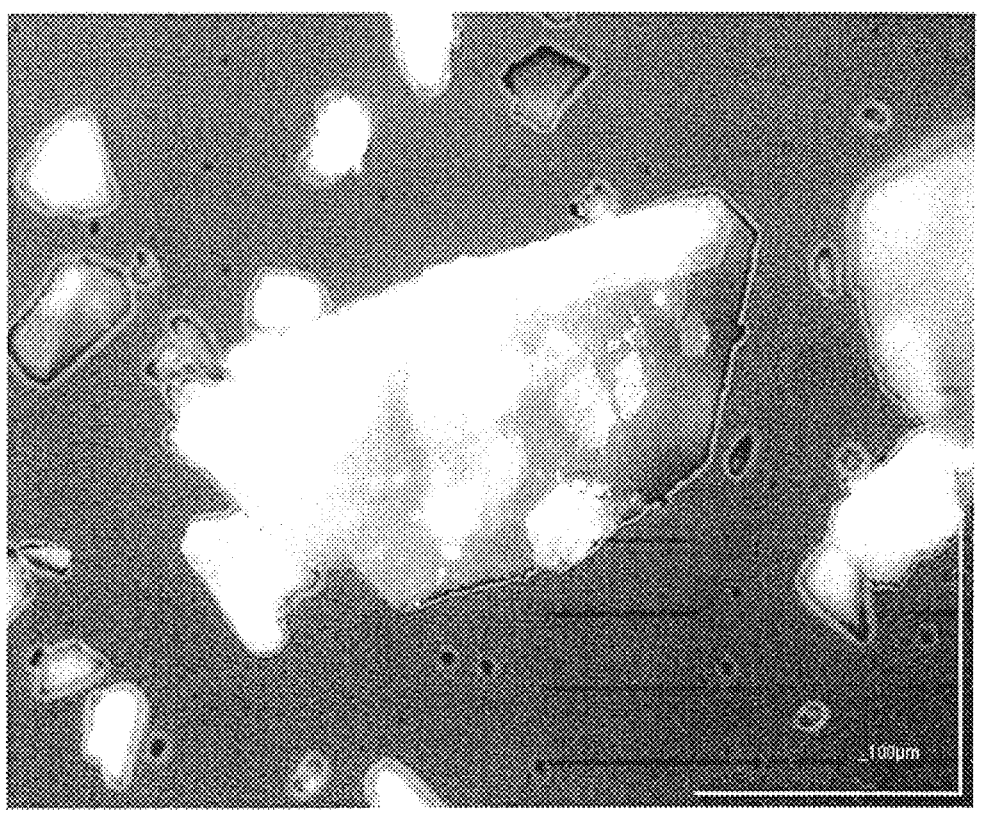
FIG. 1 is a microscopic picture of dehydrated dextrose monohydrate. The picture is taken with a Leica Microscope Type DMRB equipped with objective PL Fluotar 10×/0.30, JVC CCD camera (KY-F55BE), external light source Leica KL 1500 for top illumination. The samples were placed on an illuminated object-glass carrier and 100× magnified. The crystal is not transparent and the light is scattered with different optical densities. By the dehydration process different internal surfaces are created and each of them scatters the light resulting in the high optical density and low transparency. The dehydrated dextrose monohydrate has a high specific surface area.
Figure 2:
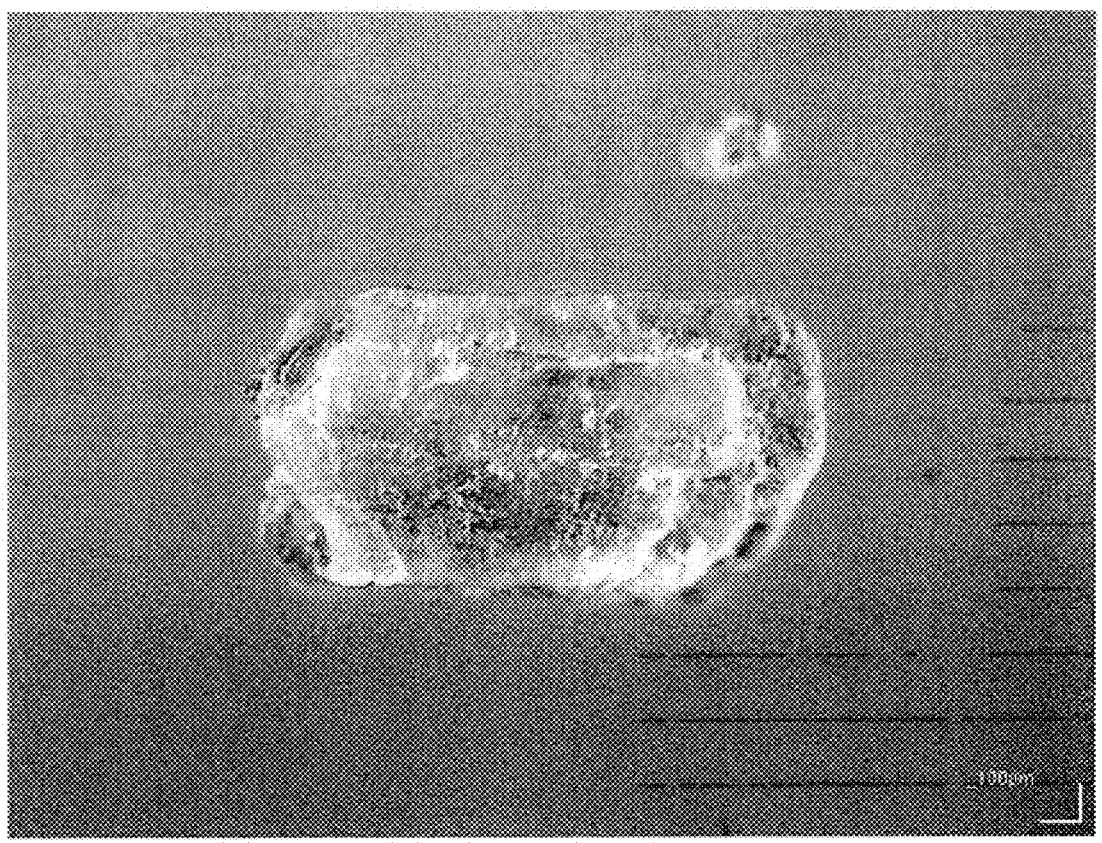
FIG. 2 is a microscopic picture of commercial anhydrous dextrose, which is produced by a crystallisation process. The crystal is highly transparent and its specific surface area is not as big as the specific surface area of dehydrated dextrose monohydrate.
Figure 3:
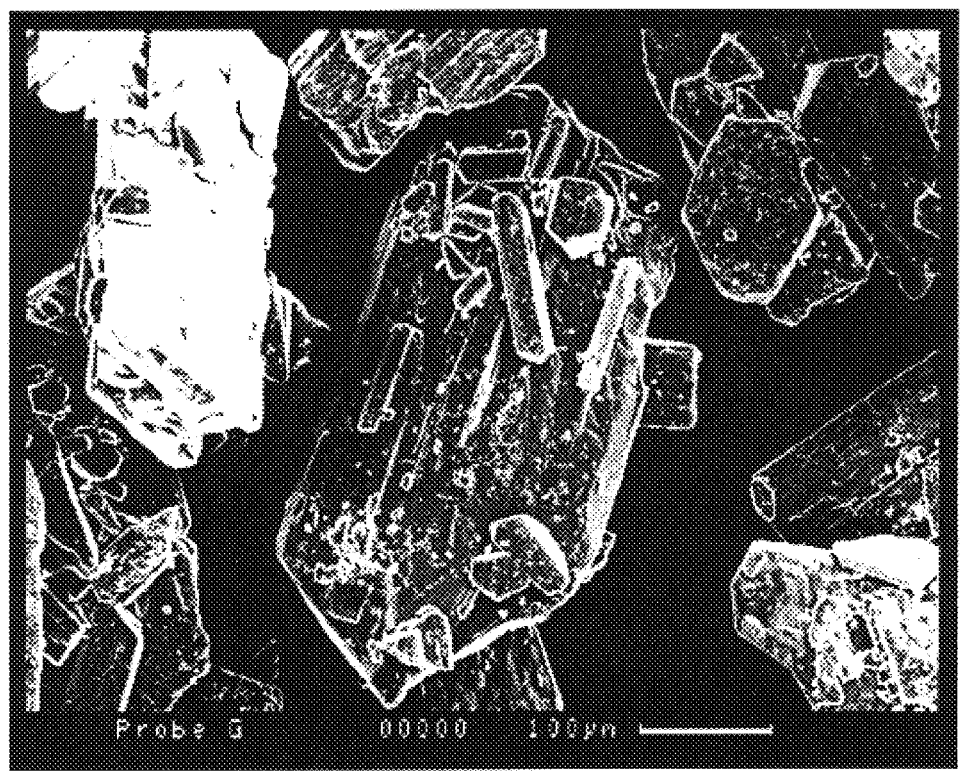
FIG. 3 is an electron microscopic picture of dehydrated dextrose monohydrate. The picture is taken with a SEM-type CamScan Cambridge S24 from gold-coated samples. The acceleration voltage was ranging from 5 to 10 kV at a magnification of 100× to 500×. By the dehydration process the macroscopic shape of the dextrose is remaining into the macroscopic shape of the monohydrate and it is not converted into the macroscopic shape of commercial anhydrous dextrose.
Figure 4:
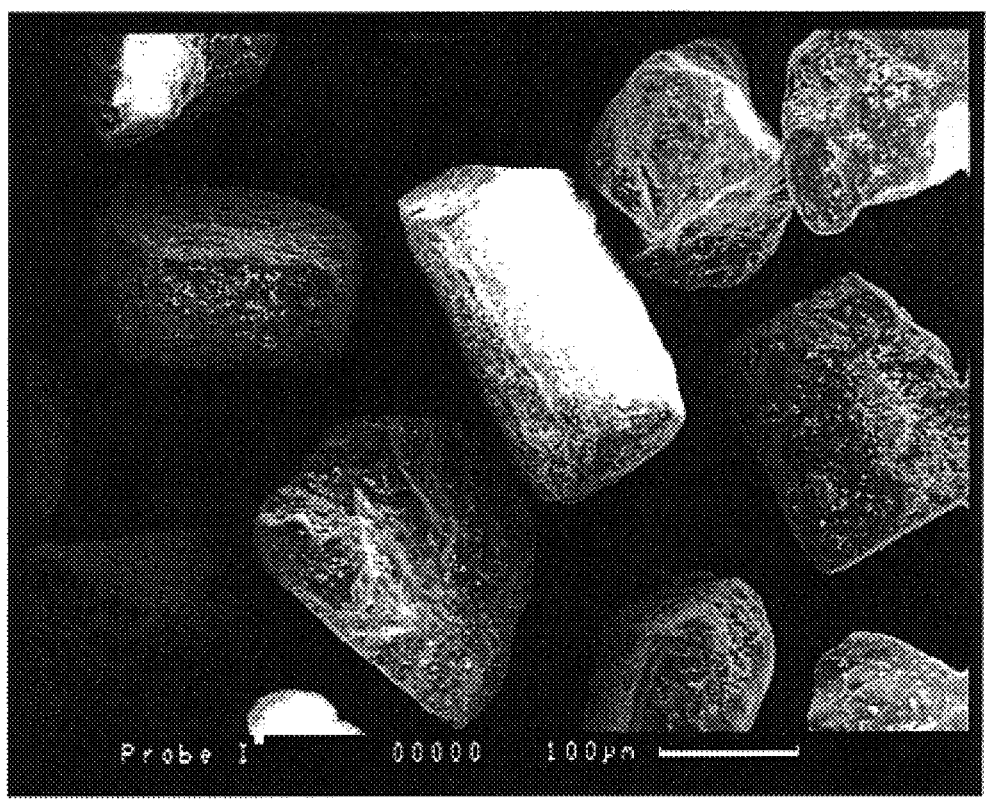
FIG. 4 is an electron microscopic picture of commercial anhydrous dextrose, produced by a crystallisation process.

The present invention relates to dehydrated dextrose monohydrate with a specific surface area of from 0.20 $m^2/g$ to 0.50 $m^2/g$ and which reduces the reaction time for preparing chemical compounds selected from the group consisting of alkyl glucoside, alkenyl glucoside, alkyl polyglucosides and alkenyl polyglucosides in a heterogeneous mixture with an alcohol.

Dehydrated dextrose monohydrate is obtained by drying dextrose monohydrate in a process comprising the following steps:

a) Taking dextrose monohydrate, b) Drying dextrose monohydrate at a temperature between 50 to 150° C., c) Collecting dehydrated dextrose monohydrate.

The dehydration (drying) of dextrose monohydrate is performed in a dryer wherein the dryer can be a fluid-bed dryer, a rotary drum-dryer, a vacuum-dryer, or a spray-dryer. However, spray-drying is not as cost-effective as the other methods for dehydration of dextrose monohydrate. The other drying methods are less energy-consuming than the spray-drying process.

At the beginning of the dehydration phase, the product temperature may not exceed 50 to 60° C. to avoid softening, lumping, and solubilisation of the dextrose monohydrate crystals. Towards the end of the drying process, the temperature can increase, but it should remain below 145 to 150° C., which is the melting temperature of anhydrous dextrose. The obtained dehydrated dextrose monohydrate has a specific surface area of from 0.2 $m^2/g$ to 0.50 $m^2/g$ and it reduces the reaction time for preparing in a heterogeneous reaction with an alcohol chemical compounds selected from the group consisting of alkyl glucoside, alkenyl glucoside, alkyl polyglucosides and alkenyl polyglucosides.

The thus obtained dehydrated dextrose monohydrate has the same melting point as the commercial available anhydrous dextrose, but there is a significant difference in the specific surface area of the two products. The commercial crystallised anhydrous dextrose has a specific surface area of about 0.04–0.06 $m^2/g$, and dehydrated dextrose monohydrate has a specific surface area of from 0.2–0.5 $m^2/g$. The specific surface area is measured with BET-method. The surface area of powdered solids or porous materials is measured with the FlowSorb 2300 by determining the quantity of a gas that adsorbs as a monomolecular layer on a sample. This adsorption is done at or near the boiling point of the adsorbate gas and the area of the sample is thus directly measurable from the number of adsorbed molecules.

The microscopic picture of dehydrated dextrose monohydrate confirms the different specific areas of dehydrated dextrose monohydrate and crystallised anhydrous dextrose. The surface of dehydrated dextrose monohydrate is not transparent due to light scattering at the different internal surfaces. The crystal of crystallised anhydrous dextrose is completely transparent, less light is scattered and thus less internal surfaces are present in the crystal.

The picture taken with the electron microscope demonstrates that by the dehydration process the macroscopic shape of the dextrose is remaining into the macroscopic shape of the monohydrate and it is not converted into the macroscopic shape of commercial anhydrous dextrose.

The production process of alkyl glucoside, alkenyl glucoside, alkyl polyglucosides and/or alkenyl polyglucosides is a heterogeneous process wherein dehydrated dextrose monohydrate is not dissolved in the liquid phase. The velocity of the heterogeneous reaction strongly depends on the particle size, but in order to exclude the influence of this parameter each time the same sieving fraction between 125 and 180 μm is taken. When excluding the influence of the particle size, the specific surface area can be important for the reactivity of the dextrose and/or the kinetics of the reaction.

By reacting dehydrated dextrose monohydrate with an alcohol in a process for preparing alkyl glucoside, alkenyl glucoside, alkyl polyglucosides and/or alkenyl polyglucosides, the reaction time is reduced significantly. The reaction time is reduced with at least 10%, preferably 20%, more preferably 25%, most preferably with 50%.

The applied reaction conditions can vary in respect of e.g. temperature, vacuum, particle size of dextrose-based product, chain length of alkyl chain of alcohol, but by keeping all the conditions constant. the dehydrated dextrose monohydrate of the current invention significantly reduces the reaction time of said process.

Example 2 demonstrates that by applying the sieve-fraction of particle size between 125 to 180 μm of dehydrated dextrose monohydrate and having a specific surface area of about 0.25–0.30 $m^2/g$, the process needs a reaction time of only 3.5 hours. The process with anhydrous dextrose (comparative example 1) or dried glucose syrup (containing at least 95% dextrose—comparative example 2) needs a reaction time of at least 4.6 hours and 5.4 hours, respectively.

In this process the alcohol can have an alkyl or alkenyl chain length selected from the group consisting of $C_1$ to $C_{30}$ and mixtures thereof.

The present invention further relates to a process, which is comprising the following steps:

a) adding dehydrated dextrose monohydrate to an alcohol containing liquid for obtaining a heterogeneous mixture, b) Stirring the heterogeneous mixture, c) Heating under vacuum to a temperature between 60° C. to 180° C., preferably between 80° C. and 150° C., more preferably between 95° C. to 120° C., d) Adding acid catalyst, e) Continuing stirring at high temperature under vacuum until level of residual dehydrated dextrose monohydrate is below desired value, (the desired value is between 0.2% and 1% based on total weight of complete reaction medium), f) Optionally neutralising of acid catalyst, and g) Optionally evaporating the excess of fatty alcohol.

The process can be run in batch or as a continuous process.

The heterogeneous mixture can be obtained either by adding in one portion dehydrated dextrose monohydrate to the alcohol containing liquid, or only part of the total amount of dehydrated dextrose monohydrate is added to the alcohol containing liquid at the beginning, and during the reaction further dehydrated glucose monohydrate is added in portions. Furthermore, the sequence of addition is not important. The alcohol containing liquid and acid can be added to the dehydrated dextrose monohydrate followed by heating. In fact steps a) to d) can be reverted or can occur at the same time.

The alcohol containing liquid can be exclusively an alcohol-phase or in cases wherein the alcohol is not liquid at the reaction temperature of the acetalisation reaction and/or wherein the heterogeneous mixture is too viscous for good kinetics at the reaction temperature, the alcohol is diluted with a liquid. Such a liquid is a typical solvent for the alcohol but the dextrose is not soluble. Typical examples of such liquids are hexane, cyclohexane, benzene, toluene, and the like.

The alcohol can be a pure product or a mixture of different alcohols wherein the alkyl or alkenyl chain length is from $C_1$ to $C_{30}$, preferably from $C_1$ and $C_{25}$, more preferably from $C_6$ and $C_{25}$, most preferably from $C_8$ and $C_{18}$.

The difference between the alkyl and the alkenyl chain is the fact that the alkenyl chain is containing an unsaturated bond.

The reaction for producing alkyl glucosides, alkenyl glucosides, alkyl polyglucosides and/or alkenyl polyglucosides is effected in presence of an acid catalyst wherein the choice of the type of acid catalyst is not particularly critical. Said acid catalyst can be a liquid acid catalyst or a solid catalyst, which can either be dissolved or dispersed in the fatty alcohol. Suitable acid catalysts include strong mineral acids such as hydrochloric acid, sulphuric acid, nitric acid, phosphoric acid, hypophosphorous acid, strong organic acids such as para-toluene sulphonic acid, methane sulphonic acid, trifluoromethane sulphonic acid, dodecylbenzene sulphonic acid, sulfosuccinic acid and the like.

The weight ratio of dehydrated dextrose monohydrate to alcohol can be from 1:2 up to 1:10, preferably from 1:2 up to 1:8, more preferably from 1:3 to 1:5. If a ratio of dehydrated dextrose monohydrate to alcohol below 1:2 is employed, then the reaction mixture may thicken after cooling down to room temperature. At the other extreme, when employing a ratio of dehydrated dextrose monohydrate to alcohol higher than 1:10, the volume requirements become excessive so that considerable reactor productivity is lost.

The liquid, which is used for dissolving the insoluble long chain fatty alcohol at the reaction temperature, and which is further used for dispersing the dehydrated dextrose monohydrate is applied in a weight ratio of dehydrated dextrose monohydrate to liquid of from 1:1 and 1:4.

The reaction mixture is heated to a temperature between 60° C. and 180° C., preferably between 80° C. to 150° C., more preferably between 95° C. and 120° C., while vacuum is applied. Higher temperatures will result in undesired by-products.

The acetalisation reaction is continued at high temperature under vacuum, and the formed reaction water is removed simultaneously. The heating is stopped when the residual amount of dehydrated dextrose monohydrate has reached desired value. The desired value varies according to the requirements of the final product in application and should be between 0.2% and 1% residual dextrose based on the total weight of the complete reaction medium. Products which need to be colour-stable at high temperature and/or alkaline conditions have a low residual level of dextrose. Consequently, the desired value of these products should be not higher than 0.25%. The measurement of the residual dextrose is based on a classical DE-method, which is a redox-titration for measuring reducing ends.

The acid can be neutralised prior to cooling down, or the product can be kept as such without neutralisation of the acid. The acid catlalyst can be neutralised before or after cooling and the residual excess of fatty alcohol can be removed by distillation. In order for obtaining a final product with a high polymerisation degree, which might be required in special applications, part of the fatty alcohol can be removed prior to catalyst neutralisation and the reaction is further proceeding at high temperature.

The current invention further relates to a process wherein:

a) 1 weight-part of dehydrated dextrose monohydrate is added to from 2 to 10 weight parts of $C_6$–$C_{25}$ alcohol for obtaining a heterogeneous mixture, b) The heterogeneous mixture is heated to a temperature between 80° C. to 180° C., while stirring under vacuum between 5 to 400 mbar, c) 0.2 to 5% w/w (based on dry substance of dehydrated dextrose monohydrate) acid catalyst is added, d) Continuing stirring at high temperature and under vacuum until the amount of residual dehydrated dextrose monohydrate is below a desired value.

The process is proceeding under dry reaction conditions and during the reaction, the formed reaction water is removed by applying vacuum. Applying commercially available dextrose monohydrate for the production of the chemical compounds requires dehydration prior to the actual acetalisation reaction. The dehydration requires a considerable time and the reactor is occupied not efficiently. At least 10%, or 20%–25%, up to 40% or even 50% of the reaction time is used for the dehydration, and as such the productivity is reduced by the same factor. Applying for the production of the aforementioned chemical compounds dry reagents avoids the occupation of the reactor for the dehydration and the productivity can improve.

Applying in the process dehydrated dextrose monohydrate of the current invention and taking the sieve-fraction between 125 and 180 μm, needs only 3.5 hours until the amount of residual dehydrated dextrose monohydrate is below 0.25%.

In a comparative example with the sieve fraction between 125 and 180 μm of commercially available crystallised anhydrous dextrose it is demonstrated that at least 4.6 hours are needed to reduce the residual dextrose level below 0.25%. Applying dried glucose syrup (containing at least 95% dextrose) needs a reaction time of 5.4 hours for obtaining a reaction mixture wherein the residual dextrose level is below 0.25%.

By applying the same sieve fraction, the influence of the particle size is excluded and the difference in velocity cannot be related to a potential difference in particle size. In fact, by applying dehydrated dextrose monohydrate said reaction time is reduced with at least 10%, preferably 20%, more preferably 25%, most preferably with 50%.

By applying dehydrated dextrose monohydrate the reaction time is reduced from at least 4.6 hours to 3.5 hours, that corresponds to a reduction of reaction time of at least 24%. Using dehydrated dextrose monohydrate instead of dried glucose syrup reduces the reaction time from 5.4 hours to 3.5 hours, which corresponds to a reduction of reaction time of at least 35%.

Application of dehydrated dextrose monohydrate gives significant advantages:
a) The reaction time of the process for preparing in a heterogeneous reaction chemical compounds with dehydrated dextrose monohydrate is significantly shorter than the reaction time of the process with commercial available anhydrous dextrose or dried glucose syrup, when applying the same particle size.
b) The short reaction time reduces the by-product formation. The reaction velocity is increased and the potential formation of all kinds of by-products is reduced significantly. The formation of products such as polydextrose and especially coloured bodies is reduced.
c) The colour of the final product is much better when applying dehydrated dextrose monohydrate of the current invention instead of commercial crystallised anhydrous dextrose. This improved colour is even more pronounced after evaporation of the liquid and the excess of alcohol. It is obvious that for certain applications the optional bleaching step for improving the colour can be excluded.
d) The capacity or throughput of the reactor is increased with a factor of at least 10%, preferably 20%, more preferably more than 25%, up to 40% or even 50% when applying dehydrated dextrose monohydrate instead of dextrose monohydrate.
e) Drying dextrose monohydrate in a fluid-bed dryer, a rotary drum-dryer, a vacuum-dryer is much cheaper than applying the acetalisation reactor for this purpose, and consequently the overall process of the current invention is much cheaper than the process wherein dextrose monohydrate is directly used in the acetalisation reactor.

The advantages of the process of the present invention will appear from the following examples.

EXAMPLE 1

Dehydration of Dextrose Monohydrate.

1. Dehydration with Fluid-bed Dryer

Dextrose monohydrate was brought in a fluid bed dryer (Retsch Type TG1) wherein the ratio of air (in kg) to product (in kg) is 0.77. The product which contained about 9% of moisture was dried to obtain dehydrated dextrose monohydrate which contained less than 0.5% water. The total driving time was about 25 to 70 minutes at a temperature of the incoming air of between 90° C. and 120° C.

2. Dehydration with Turbo-dryer

Dextrose monohydrate was brought in a horizontal-placed turbo-dryer (VOMM, Mailand, Italy). The dehydration occurred at a temperature of between 90 to 150° C. in a stream of air of 5 Normalised $m^3$/kg (i.e volume of gas at 0° C. and 1 mbar) dextrose and a rotation speed of 1200 $min^{-1}$.

EXAMPLE 2

Preparation of Chemical Compounds with Dehydrated Dextrose Monohydrate.

In a 3-necked reaction vessel equipped with thermometer, stirrer, distillation column and vacuum-connection was brought 1 part of dehydrated dextrose monohydrate (sieve fraction between 125 and 180 μm) and 4.36 parts of a $C_{12}$–$C_{14}$ mixture of fatty alcohols. The heterogeneous mixture was heated from 30° C. to 105° C. in 30 minutes at a vacuum of 28 to 30 mbar, while stirring. 1% (based on dry substance of dextrose) of para-toluene sulphonic acid was added to start the reaction. The reaction was continued until the quantity of residual dextrose, as measured by the DE-method, was below 0.25% (based on weight of the total reaction mixture). The reaction time was 3.5 hours.

Comparative Example 1

Preparation of Surface Active Compounds with Crystalline Anhydrous Dextrose 1 part of crystalline anhydrous dextrose (C☆Dex 02402) (Cerestar) (sieve fraction between 125 and 180 μm) was used. The procedure as described in example 2 was followed. The reaction time was 4.6 hours.

Comparative Example 2

Dehydration of Glucose Syrup (Dextrose Content 96%).

A glucose syrup C☆SWEET D 02763 Cerestar) (dry substance ca. 70%) was sprayed at a flow rate of 7 kg/h at 70° C. into a Niro FSD pilot plant spray dryer. For powdering ca. 9 kg coarsely milled dried product at a ratio liquid/solid of 1:2 was added. The atomising conditions were as follows:

| | |
|---|---|
| Air temperature: | 20° C. |
| Air pressure: | 3 bar |
| Air flow: | 20 kg/h |
| Diameter nozzle: | 2 mm |
| Air valve position: | −0.5 mm |
| The drying chamber was operated at: | |
| Pressure chamber: | −10 mm WG |
| Pressure difference first cyclone: | 90 mm WG |
| Air flow: | 520 kg/h |
| Air inlet temperature: | 146° C. |
| Air outlet temperature: | 81° C. |
| The fluid bed was adjusted to: | |
| Pressure difference air inlet pipe: | 22 mm WG |
| Air flow: | 120 kg/h |
| Air inlet temperature: | 79° C. |
| Powder temperature: | 75° C. |
| Powder bed pressure: | 60–75 mm WG |

Preparation of Surface Active Compounds with Dried Glucose Syrup.

1 part of spray dried glucose syrup (sieve fraction between 125 μm and 180 μm) was used. The procedure as described in example 2 was followed. The reaction time was 5.4 hours.

What is claimed is:
1. A dehydrated dextrose monohydrate characterized in that it has a specific surface area of from 0.20 $m^2$/g to 0.50

$m^2/g$ and it reduces the reaction time for preparing a chemical compound selected from the group consisting of alkyl glucoside, alkenyl glucoside, alkyl polyglucosides and alkenyl polyglucosides in a heterogeneous mixture with an alcohol.

2. The dehydrated dextrose monohydrate according to claim 1, wherein said reaction time is reduced by at least 10%.

3. The dehydrated dextrose monohydrate according to claim 1, wherein said reaction time is reduced by at least 20%.

4. The dehydrated dextrose monohydrate according to claim 1, wherein said reaction time is reduced by at least 25%.

5. The dehydrated dextrose monohydrate according to claim 1, wherein said reaction time is reduced by at least 50%.

6. A dehydrated dextrose monohydrate according to according to claim 2, wherein the chemical compound is an alkylglucoside or a mixture comprised of alkylpolyglucosides.

7. A dehydrated dextrose monohydrate according to claim 3, wherein the chemical compound is an alkenylglucoside or a mixture comprised of alkenylpolyglucosides.

8. A process for preparing a chemical compound selected from the group consisting of alkyl glucoside, alkenyl glucoside, alkyl polyglucosides and alkenyl polyglucosides in which an alcohol represented by ROH in a heterogeneous mixture reacts with a dehydrated dextrose monohydrate according to claim 1, wherein R corresponds to the alkyl or alkenyl moiety in the glucoside or polyglucosides.

9. The process to claim 8, wherein a R moiety has a chain length of $C_1$ to $C_{30}$.

10. The process according to claim 8 or 9, wherein said process comprises:
    a) adding dehydrated dextrose monohydrate to a fatty alcohol containing liquid to obtain a heterogeneous mixture,
    b) stirring the heterogeneous mixture,
    c) heating the heterogeneous mixture under vacuum to a temperature between 60° C. to 180° C.,
    d) adding acid catalyst,
    e) continuing stirring at high temperature under vacuum until a level of residual dehydrated dextrose monohydrate is below a desired value,
    f) optionally neutralizing the acid catalyst, and
    g) optionally evaporating the excess of fatty alcohol.

11. The process according to claim 10, wherein in c) the temperature is 80° C. to 150° C.

12. The process according to claim 10, wherein in c) the temperature is 95° C. to 120° C.

13. The process to claim 8 or 9, wherein:
    a) 1 weight-part of dehydrated dextrose monohydrate is added to from 2 to 10 weight-parts of $C_6$–$C_{25}$ alcohol for obtaining the heterogeneous mixture,
    b) the heterogeneous mixture is heated to a temperature of between about 80° C. to 180° C., while stirring at 5 to 400 mbar vacuum,
    c) 0.2 to 5% w/w acid catalyst is added, based on dry substance of dehydrated dextrose monohydrate, and
    d) stirring is continued at high temperature and under vacuum until the level of residual dehydrate dextrose monohydrate is below a desired value.

14. The process according to claim 10, wherein the liquid comprises a non-polar solvent for the alcohol under the conditions in the acetalization reaction.

15. The process according to claim 10, wherein the liquid comprises a hydrocarbon solvent.

16. The process according to claim 10, wherein at least one of the ratio of dehydrated dextrose monohydrate to alcohol or the point of neutralization is selected or adjusted so that a glucoside or a mixture of comprised of glucosides is obtained.

17. A process according to claim 8, wherein the polymerization degree is increased so that a mixture comprised of polyglucosides is obtained.

18. A process according to claim 8, wherein an alkylglucoside or a mixture comprised of alkylpolyglucosides is obtained.

19. A dehydrated dextrose monohydrate according to claim 8, wherein an alkenylglucoside or a mixture comprised of alkenylpolyglucosides is obtained.

20. A process for preparing dehydrated dextrose monohydrate by drying dextrose monohydrate under conditions such that said dehydrated dextrose monohydrate has a specific surface area of from 0.20 $m^2/g$ to 0.50 $m^2/g$ and it reduces the reaction time for preparing, in a heterogeneous reaction with said dehydrated dextrose monohydrate and an alcohol, a chemical compound selected from the group consisting of alkyl glucoside alkenyl glucoside, alkyl polyglucosides and alkenyl polyglucosides, said process comprises:
    a) providing dextrose monohydrate,
    b) drying dextrose monohydrate at a temperature between 50 to 150° C., and
    c) collecting said dehydrated dextrose monohydrate.

* * * * *